United States Patent [19]

Sato

[11] 4,145,415

[45] Mar. 20, 1979

[54] PHYSIOLOGICALLY ACTIVE SUBSTANCES AND THE ISOLATION THEREOF

[76] Inventor: Akihiko Sato, 11-18, Minoh 8-chome, Minoh, Japan

[21] Appl. No.: 845,426

[22] Filed: Oct. 25, 1977

[30] Foreign Application Priority Data

Oct. 30, 1976 [JP] Japan .............................. 51-130741

[51] Int. Cl.² .................... A61K 35/78; A61K 31/715
[52] U.S. Cl. .................................... 424/195; 424/180
[58] Field of Search ............................... 424/195, 180

[56] References Cited

FOREIGN PATENT DOCUMENTS 51-17166 5/1976 Japan.

*Primary Examiner*—Donald B. Moyer
*Attorney, Agent, or Firm*—Hubbell, Cohen, Stiefel & Gross

[57] ABSTRACT

Disclosed are three new active substances possessing activity in mammals for improving or curing hepatic diseases, antitumor activity upon oral administration or anti-inflammatory activity. These substances were isolated from *Ganoderma lucidum* (Fr.) Karst.

10 Claims, 4 Drawing Figures

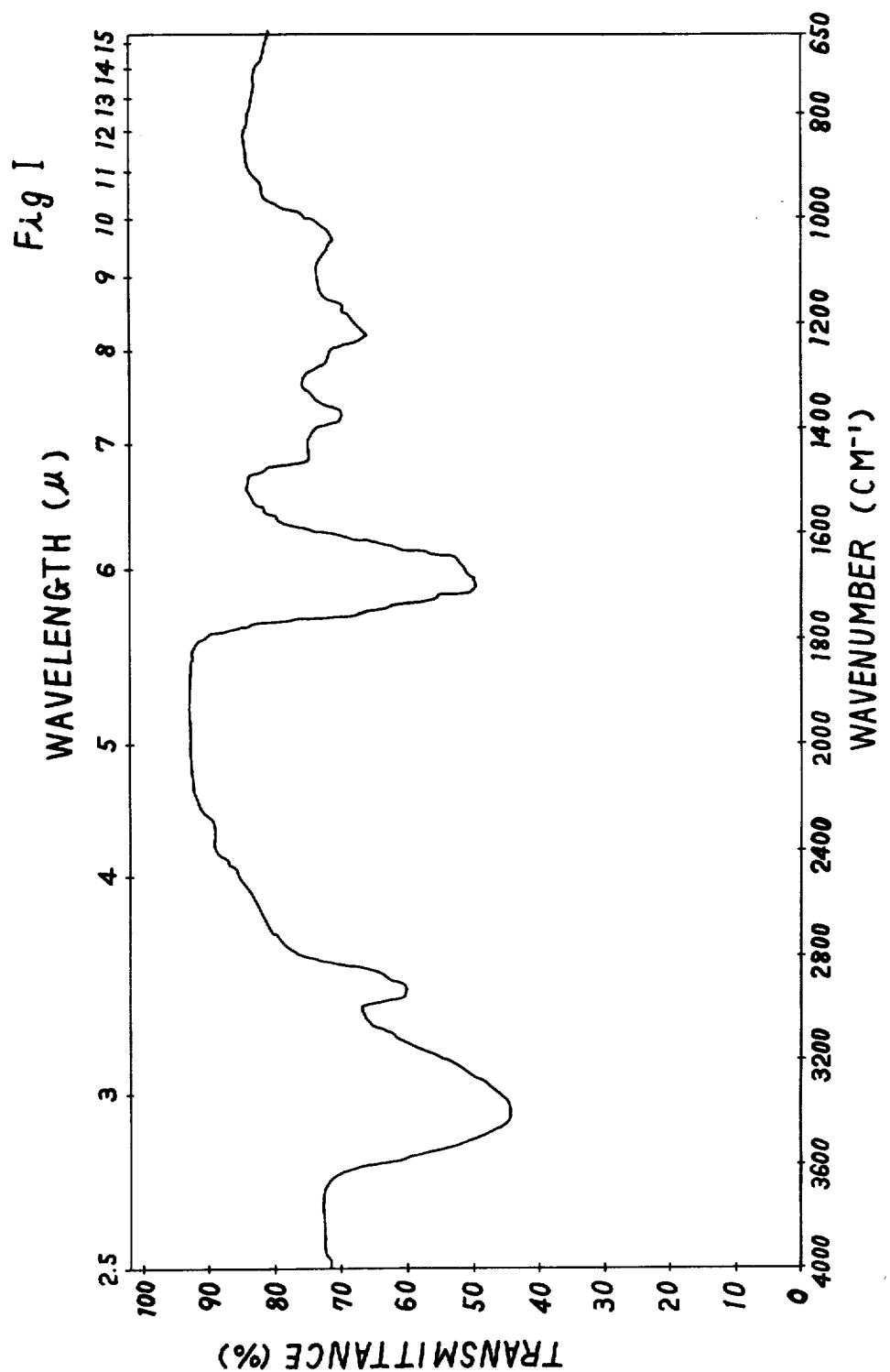
Fig I

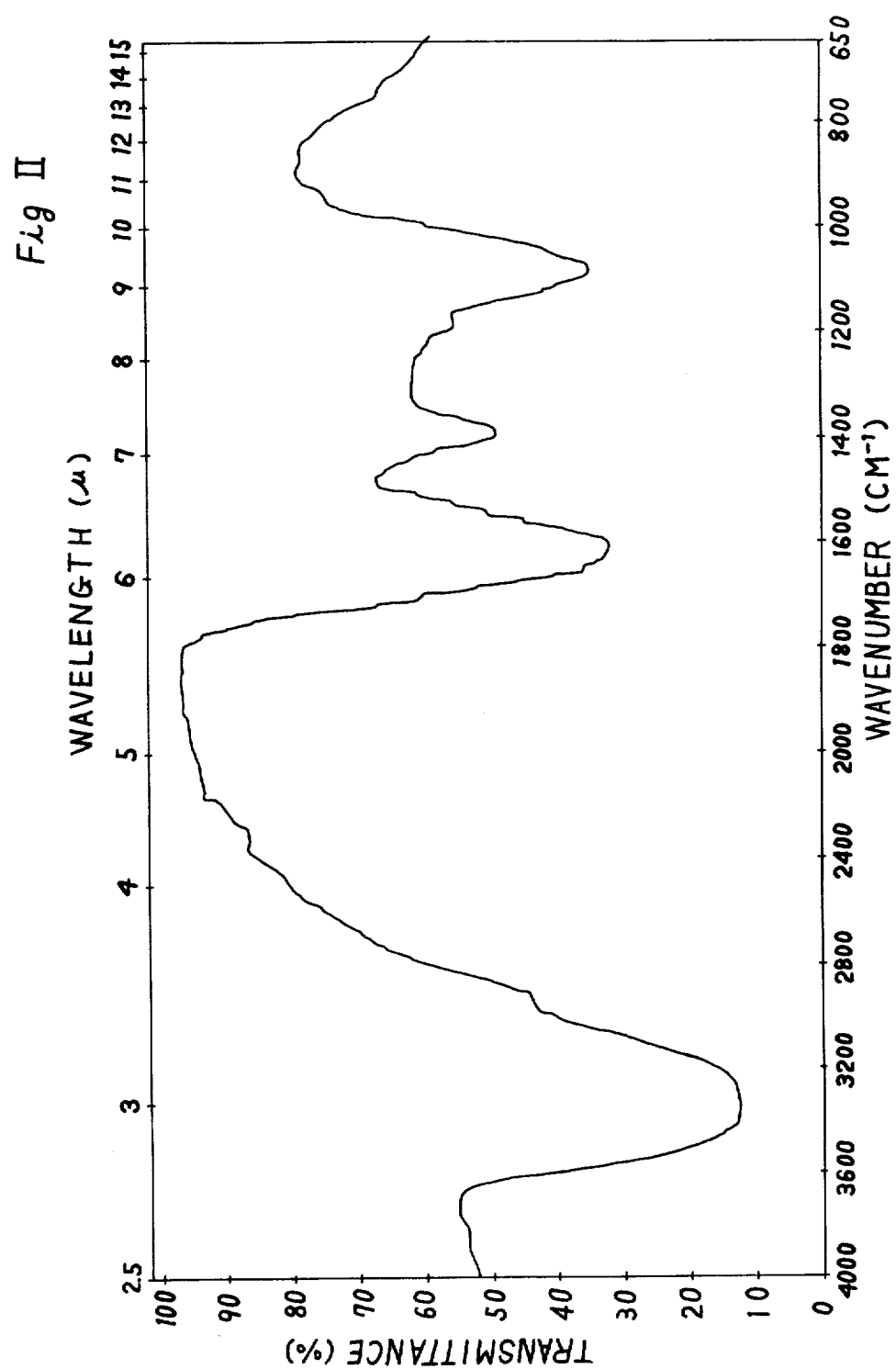

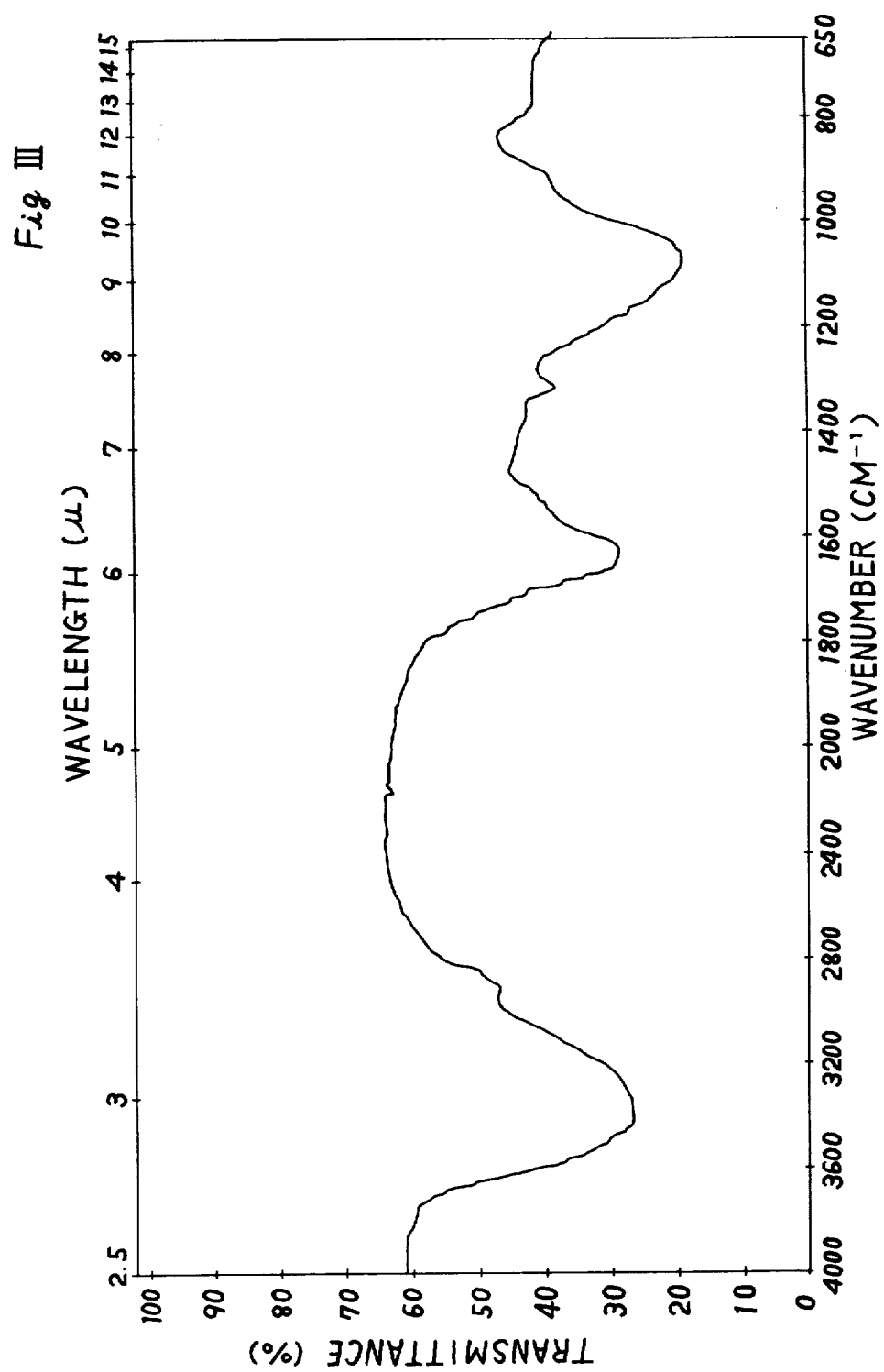
Fig III

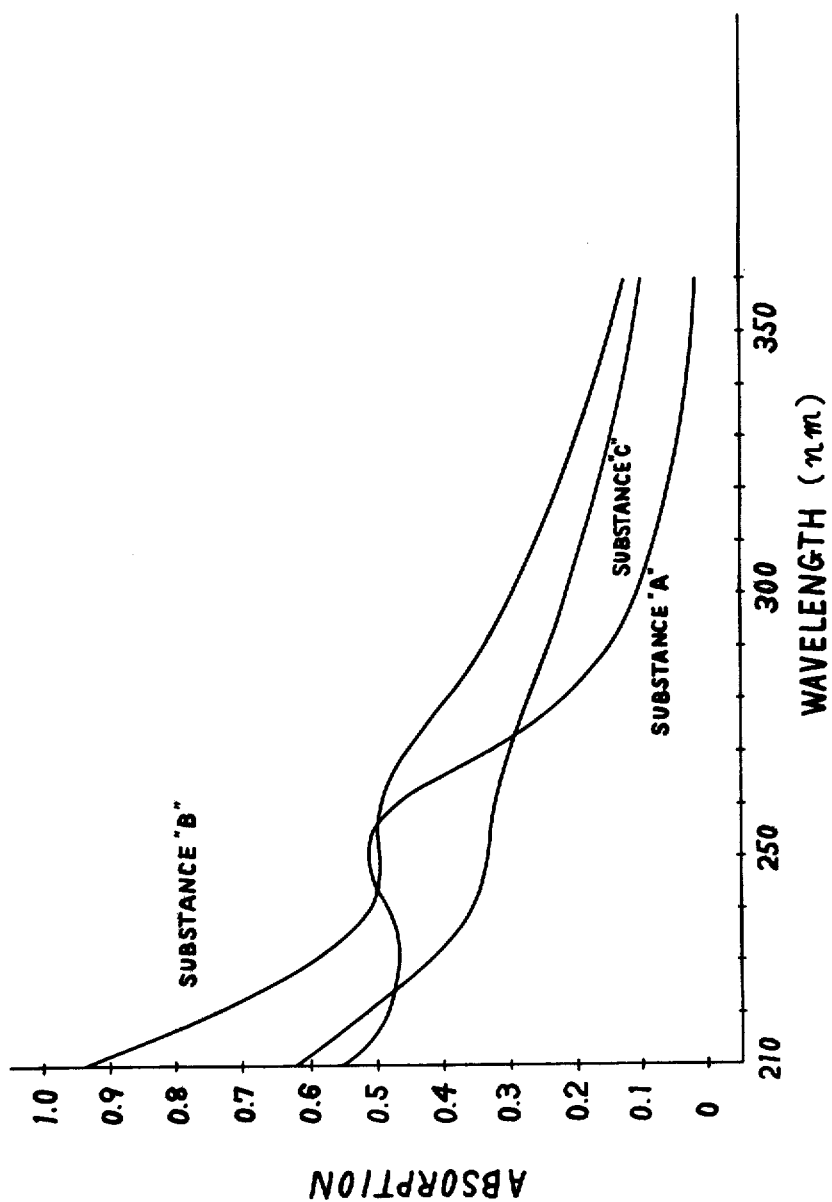

PHYSIOLOGICALLY ACTIVE SUBSTANCES AND THE ISOLATION THEREOF

BACKGROUND OF THE INVENTION

1. Field of the Invention

This invention relates to novel substances useful as medicines and which are isolated from the fungus, "*Ganoderma lucidum* (Fr.) Karst" of the group Polyporaceae.

2. Description of the Prior Art

"*Ganoderma lucidum* (Fr.) Karst" which is used as the starting material for this invention is called, Mannentake or Reishi in Japan, where it has long been used as an "elixir of life". It is said that this fungus is also effective in cancer diseases. When used as a decoction, a very large quantity must be drunk in order to obtain the desired effect, because of the different kinds of active substances present in Mannentake and therefore, methods for the isolation of active substances therefrom has long been desired.

There have been known methods for isolating antitumor substances from *Grifola albicans* Imazeki, *Lampteromyces japonics* Sing, *Flammulina velutipes* Sing, *Trametes cinnabarina* Fr., *Grifola frondosa* S. F. Gray, *Coriolus versicolor* Quel, *Elfvingia applanata* Karst, *Lentinus edodes* Sing, *Inonotus sciurinus* Imazeki, *Phellinus yucatensis* Imazeki, *Ganoderma boninense* Pat. and the like (see Japanese Patent Publication Nos. 37-18196, 39-13765, 39- 13380, 40-2045, 43-16047, 43-25563, 46-16911, 46-17149, 46-21664, 48-8489, 48-80371, 49-24211, 49-32931, 51-17166, 51-36322) and also methods for preparing antitumor substances by cultivating of *Lampteromyces japonics* Sing, *Flanmnulina velutipes* Sing, *Phellinus yucatensis* Imazeki, *Coriolus versicolor* Quel and the like (see Japanese Patent Publication Nos. 44-6634 and 46-16912, Japanese Provisional Patent Publication Nos. 48-40997, 49-35588 and 49-48896).

However, any the isolation from mannentake of an antitumor substance especially effective in oral administration has not been reported prior to this invention. The known antitumor substances referred to in the above citations are generally polysaccharides. The antitumor substance of this invention is also a polysaccharide but is peculiar in its antitumor activity in vivo.

The known polysaccharide antitumor substances are generally ineffective in in vitro antitumor tests and effective in vivo only in the case of intraperitoneal administration. In contrast, the antitumor substance of this invention is effective in in vitro tests as well as in in vivo tests in the case of oral administration. Accordingly, it is considered that the known polysaccharides when injected intraperitoneally act on a cancer system of the host via its immunity system, while the antitumor substance of the invention when administered orally, acts on a cancer system via the immunity system too but also possesses cytotoxicity against cancer cells. It is therefore believed that due to the difference in pharmacological properties, the chemical structure of the present antitumor substance is clearly different from that of the known polysaccharide antitumor compounds.

SUMMARY OF THE INVENTION

According to invention, there is provided a process for isolating physiologically active substances which comprises extracting *Ganoderma lucidum* (Fr.) Karst with water under boiling, concentrating the water extract under reduced pressure, extracting the resulting condensate with an organic solvent, preferably at ambient temperature or under cooling, to separate from the extract a substance "A," and further treating the insoluble portion with an aqueous organic solvent, preferably at ambient temperature or under cooling, to separate a substance "B" which is soluble in said solvent and a substance "C" which is insoluble in said solvent.

It has been found that the substances "A," "B" and "C" obtained by the process of the invention are useful as medicines and especially "A" possesses an activity ameliorating or curing hepatic diseases, "B" has antitumor activity and "C" has anti-inflammatory activity.

DESCRIPTION OF THE PREFERRED EMBODIMENTS

*Ganoderma lucidum* (Fr.) Karst may be used whole, or any of the fruit body, mycelium or spore thereof may be used. Its well dried fruit is preferred for use, because when used raw, it may sometimes reduce the yield of the object substances upon decomposition. The starting material may be of any sort without distinction as to growing districts and shape. It is preferred to use those which are artificially cultured, and the wild products produced at Odawara in Kanagawa Prefecture; Minabemura in Wakayama Prefecture; Yoro-gun in Gifu Prefecture; Minamimuro-gun in Mie Prefecture; Tanigawadake in Gunma Prefecture; Hakusan district in Ishikawa Prefecture; Mikata district in Fukui Prefecture; Harimoriyama in Nagano Prefecture; Shirouma district in Nagano Prefecture, all in Japan are most preferred. It was found that those harvested, especially from June to September give a good result.

In solution, the harvested and dried *Ganoderma lucidum* (Fr.) Karst is extracted with boiling water. The material is preferably cut in small pieces in order to make the extraction easy. By such pretreatment, the efficiency of the extraction is increased.

The more the quantity of water used in the extraction, the better the results, but a quantity of 50~80 fold of water on a weight basis is appropriate from the viewpoint of after-treatment.

The extraction with water is usually conducted under boiling for three hours or more, preferably for three to five hours. Then, the extract, after filtration, is concentrated under reduced pressure, preferably at a temperature below 60° C., to dryness. Such concentration may however stop at 1/5~1/10 of the original volume. The dried extract showed 30~40% of tumor inhibitory rate in an animal test.

The extract is further treated with an organic solvent. A lower aliphatic alcohol (e.g., ethanol, methanol, i- or n-butanol), benzene, xylene, toluene, chloroform, ethyl ether, acetone and the like may be used as the organic solvent. The preferred solvent is a lower aliphatic alcohol. The most preferred one is 98% or more ethanol. The extraction is conducted usually at ambient temperature or under cooling, e.g., to 4° C.

A soluble portion and an insoluble portion can be separated, e.g., by filtration. The soluble portion is concentrated preferably below 60° C. and under reduced pressure to obtain the substance "A."

The substance "A" may be purified by subjecting it to e.g., column chromatography, if desired.

Then the insoluble portion is treated with an aqueous organic solvent to separate it into a soluble portion and an insoluble portion. As the organic solvents used herein there may be mentioned organic solvents miscible with water such as a lower aliphatic alcohol (e.g., methanol, ethanol, i- or n-butanol), acetone, dioxane, tetrahydrofuran, dimethylformamide, dimethylsulfoxide or the like, the lower aliphatic alcohol, especially ethanol, being preferred. The water content of the organic solvent is usually 20~50%, preferably 20~30%, although it may be different depending on the organic solvent used. The treatment is usually conducted at ambient temperature or under cooling and the resulting mixture is filtered to separate a soluble portion and an insoluble portion.

The soluble portion is concentrated, preferably under reduced pressure, and below 60° C. to obtain the substance "C."

The substances "B" and "C" may be purified by column chromatography, salting out or fractional solution using the aqueous organic solvent as mentioned above, if desired.

In one aspect, this invention provides a pharmaceutical composition which comprises any of the substances of the invention, together with a pharmaceutically acceptable carrier therefor.

Such compositions may be in a form suitable for oral, parenteral or topical use. The preferred forms are tablets, capsules and powders. Solid carriers may be starch, talc, lactose, dextran and the like. Binders, colors, flavors, preservatives, disintegrants and the like may be added to the compositions in accordance with conventional pharmaceutical practice.

The oral dosage of substance "B" will usually be between 3~5 g/day for adults divided into three doses. The oral dosage of the substance "A" or "C" will usually be between 0.5~1.5 g/day for adults also in three divided doses.

The following examples illustrate the invention.

EXAMPLE 1

5 kg of well dried fruit of wild *Ganoderma lucidum* (Fr.) Karst which was harvested at Odawara in Kanagawa Prefecture in Japan were broken into small pieces and boiled in 60 times in weight of water based on the weight of the fruit body. The hot mixture was filtered and the filtrate was concentrated below 60° C. and in vacuo to dryness.

500 g of the resulting extract powder were extracted with 10 times the weight of 99.9% ethanol based on the weight of the powder at ambient temperature for 3 hours, three times, and then allowed to stand for 48 hours. The mixture was filtered to separate it into an insoluble portion (I) and a filtrate, the latter of which was concentrated below 60° C. and in vacuo to obtain 90 g of dried powder (Substance "A"). 410 g of the insoluble portion (I) were further extracted with 20 time its weight of 30% ethanol at ambient temperature while stirring, three times and then allowed to stand for 48 hours. The mixture was filtered to separate it into an insoluble portion (II) and a filtrate. The filtrate was concentrated below 60° C. and in vacuo to yield 280 g of dry brown powder (Substance "B").

Further, the insoluble portion (II) was dried at below 40° C. and in vacuo to obtain 130 g of blackish-brown powder (Substance "C").

EXAMPLE 2

5 kg of well dried fruit body as used in Example 1 were broken into small pieces and boiled in 60 times its weight of water for 3 hours. The extract was filtered to obtain 280 liters of a filtrate, which was concentrated below 60° C. to 28 liters. The concentrate was stirred with 220 liters of 99% ethanol and filtered. 5 liters of 30% ethanol were added to the precipitate and stirred under cooling. Then the residue obtained by filtration was again extracted with 5 liters of 30% ethanol. The extracts were filtered and the filtrate was concentrated in vacuo to obtain 200 g of a white powder (Substance "B").

Thus substance "A" of *Ganoderma lucidum* (Fr.) Karst is a crystalline powder and has the following characteristics:

(i) it possesses activity in ameliorating or curing hepatic diseases, (ii) when present in a KBr disc, it has a characteristic infra-red spectrum which has absorption maxima at, inter alia, about 3400, 2950, 1700, 1380, 1220 and 1040 cm$^{-1}$ (see FIG. I), (iii) in ethanol solution, it has a characteristic ultraviolet spectrum with absorption maxima, one of which is at about 253 nm (see FIG. IV), (iv) when run on Kiesel-gel using a 9:1 mixture of chloroform and ethanol in thin layer chromatography, the Rf values are approximately 0.29, 0.44, 0.56, 0.63, 0.73 and 0.81, (v) it is positive in a steroid coloring reaction using a reagent of 1:1 concentrated sulfuric acid and acetic acid, (vi) it is positive in an aldehyde coloring reaction using an anisaldehyde-sulfuric acid reagent, (vii) it is negative in an amino acid coloring reaction using a ninhydrin reagent, and (viii) it is soluble in water, aliphatic alcohols, chloroform, benzene, ethyl ether and acetone, The substance "B" is a powder having the following characteristics:

(i) it shows an antitumor activity when orally administered, (ii) when present in a KBr disc, it has a characteristic infra-red spectrum which has absorption maxima at, inter alia, about 3350, 1620, 1380, and 1080 cm$^{-1}$ (see FIG. II).

(iii) in aqueous solution, it has a characteristic ultra-violet spectrum with absorption maxima, one of which is at about 257 nm (see FIG. IV), (iv) it is negative in a steroid coloring reaction using a reagent of 1:1 concentrated sulfuric acid and acetic acid, (v) it is positive in an aldehyde coloring reaction using an anisaldehyde-sulfuric acid reagent, (vi) it is positive in an amino acid coloring reaction using a ninhydrin reagent, (vii) it is soluble in aqueous ethanol, sparingly soluble in ethanol and insoluble in chloroform, ethyl ether and acetone, The substance "C" is a powder and has the following characteristics:

(i) it possesses anti-inflammatory activity, (ii) when present in a KBr disc, it has a characteristic infra-red spectrum which has absorption maxima at, inter alia, about 3400, 1640 and 1060 cm$^{-1}$ (see FIG. III), (iii) in aqueous solution, it does not show any characteristic absorption maxima in the ultra-violet spectrum (see FIG. IV), (iv) it is negative in a steroid coloring reaction using a 1:1 concentrated sulfuric acid and acetic acid reagent, (v) it is negative in an aldehyde coloring reaction using an anisaldehyde-sulfuric acid reagent, (vi) it is negative in an amino acid coloring reaction using a ninhydrin reagent, (vii) it is soluble in water and aqueous ethanol, and insoluble in ethanol, chloroform, benzene, ethyl ether and acetone.

Further, the substance "B" is judged chemically to be a polysaccharide from the characteristics as mentioned above and is a substantially pure substance. "Substantially pure" a used herein means a purity of about 97% or more, preferably about 99% or more. When the substance "B" was hydrolyzed with dilute hydrochloric acid, it yielded 90% or more of glucose and 5%~7% of amino acids.

Tests methods for the pharmacological effects of the substances isolated according to the invention and the results thereof are as follows:

Antitumor Test (i) In vivo test

Solid Sarcoma 180, $1 \times 10^7$ cells were subcutaneously injected into the axillary region of each of 20 female mice weighing 20±2 g. The group of 20 mice was divided into two groups one of which was administered the substance "B" and the other being an untreated group. The administration of the substance "B" was orally conducted in a daily dose of 1 g/kg after 24 hours of the implantation of the cancer cells, twenty times. After the administration, the weight of the tumor was measured and the tumor inhibition ratio (%) was calculated by the average tumor weight of the treated group per average tumor weight of the control (untreated) group. By this method, the tumor inhibition ratio of the substance "B" was found to be 50-70%, which shows that the substance "B" is very effective orally as an antitumor agent.

On the other hand, when Kurestin (Tradename of PSK manufactured by Kureha Chemical Industry Co. in Japan, YAKUGAKU ZASSHI 96, 4, 413~424 (1976)) was testd under the same conditions as above, its tumor inhibition ratio was only 12.8 %. It is generally agreed that a drug is ineffective unless its tumor inhibition ratio is at least 25%, usually over 40%.

(ii) In vitro test

JTC-26 (cells originating from human cancer), $5 \times 10^4$/ml were implanted into MEM medium (90% of MEM and 10% of fetal calf serum), to which 1 mg/ml of the substance "B" was added. As a control, 1 mg/ml of Kurestin was added to another sample of implanted medium.

The two broths were centrifuged to collect the cells, while the cells which were attached to the culture vessel were collected by treatment with trypsin. The collected cells were combined and the number of living cells were counted. The cancer inhibition ratio was calculated by average living cell number of the drug addition group per average living cell number of control group.

The substance "B" : 76.6%
Kurestin: 8.4%

When the inhibition ratio is over 40%, a drug is deemed to be effective.

Clinical Evaluation As Antitumor Agent

Case 1

A 35 year old female patient after being operated on relapsed. Her mastocarcinoma metastasized to her whole body, and the patient complained of lumbago and loss of appetite. On the 19th of April, 1976, she was judged to have a life span not longer than about three months based on the results of multiple diagnosis including radiodiagnosis. From that date, the substance "B" of the invention was orally administered to the patient, at meal times three times a day in a dose of about 3 g/day. Lumbago due to pelvic metastasis disappeared by the 7th day and the diarrhea which she experienced also stopped. After about 2 months and a half, the patient who had been bed confined could take a walk, but did not show any change in radiophotgraphy. After about 3 months and a half, her clinical test values were improved as follows:

|  | One Month After Administration | | Three and A Half After Administration | Normal Values |
|---|---|---|---|---|
| Alkali-phosphatase | 275 | (u/L) | 71 | 30 ~ 85 |
| Glucose | 159 | (mg/dl) | 109 | 65 ~ 110 |
| Cholesterol | 158 | " | 153 | 150 ~ 300 |
| SGOT | 311 | (u/L) | 17 | 7 ~ 40 |
| LDH | 390 | " | 139 | 100 ~ 225 |
| SGPT | 519 | " | 17 | 6 ~ 53 |

Lumbago again appeared after about a half year of administration and disappeared about 3 months thereafter. The patient died after 1 year, 2 months and 22 days. She complained of loss of appetite at about 1 year after administration. Prolongation of her life using substance "B" was considered to be 11 months.

Case 2

A 32 year old male patient after operation for rectal cancer relapsed when the tumor metastasized to the pelvis. The patient complained of heavy constipation, anorexia and edema in the prelic limb due to metastasis. He was considered to have a life span of not longer than about 6 months.

From 24th June, 1975, about 3 g/day of the substance "B" were given orally to the patient at meal times three times a day. After 2 weeks, constipation, anorexia and prelic limb edema disappeared. After 4 months, the patient returned to business. He could walk after 2 months of administration of the drug. The values of his clinical tests on 15th Dec., 1975 were as follows:

|  | Test Values |
|---|---|
| WBC | $5.3 \times 10^3$ |
| RBC | $428 \times 10^4$ |
| LDH | 270 (u/L) |
| SGOT | 18 " |
| SGPT | 7 " |

In spite of continuous administration, metastasis to the breast was observed in April, 1977 with pain, and the patient died in June, 1977. Prolongation of his life is, was considered to be 1 and a half years.

Hepatic Function Test

The amount of each of Serum glutamate oxalacetate transaminase (SGOT), Serum glutamate pyruvate transaminase (SGPT) and alkalinephosphatase was measured by conventional methods.

It was found that the substance "A" is remarkably effective for strengthening hepatic function in humans. For instance, when the substance "A" was orally administered to a female patient (36 age) at 1 g/day, SGOT of 311 u/L, SGPT of 519 u/L and alkalinephosphatase of 275 u/L were reduced to 17 u/L, 8 u/L and 71 u/L, respectively, all of which are normal values.

Anti-inflammatory Test

The anti-inflammatory activity was observed by the Mizushima anti-inflammatory test method (1965). 0.3 ml of a solution of 0.1~1g of sample in 10 ml of water was mixed with 2.7 ml of a protein solution (0.75 w/v of human serum albumin V fraction in a pH 5.3 solution of 1/15 mol potassium hydrogen phosphate and 1/10 mol potassium dihydrogen phosphate), and warmed at 67° C. for 180 seconds. A drug is judged as "plus" when coagulation is stopped and dissolved.

By this method, the substance "C" was found to possess anti-inflammatory activity.

TOXICITY (a) A dried powder of a hot water extract of *Ganoderma lucidum* (Fr.) Karst showed no toxicity in mice upon oral administration of 1 g/kg for 20 days.

(b) The oral toxicity of substance "B" was examined with the doses of 100 mg~3000 mg/kg to mice daily for 15 days. No significant changes (reduction of body weight, bradypepsia, diarrhea, anemia, etc.) were observed.

Accordingly, substance "B" is an antitumor agent which has the characteristics of no substantial side effects, and the capabilities of directly attacking cancer cells when orally administered.

What I claim is:

1. A physiologically active substance "B" derived from *Ganoderma lucidum* (Fr.) Karst which is a powder having the following characteristics:
   (i) it possesses antitumor activity when orally administered,
   (ii) when present in KBr disc, it has a characteristic infra-red spectrum which has absorption maxima at inter alia about 3350, 1620, 1380 and 1080 cm$^{-1}$,
   (iii) in aqueous solution, it has a characteristic ultraviolet spectrum with absorption maxima one of which is at about 257 nm,
   (iv) it is negative in a steroid coloring reaction using a 1:1 reagent of concentrated sulfuric acid and acetic acid,
   (v) it is positive in an aldehyde coloring reaction using an anisaldehyde-sulfuric acid reagent,
   (vi) it is positive in an amino acid coloring reaction using a ninhydrin reagent,
   (vii) it is soluble in aqueous ethanol, sparingly soluble in ethanol and insoluble in chloroform, ethyl ether and acetone.

2. A process for the isolation of a physiologically active substance which comprises extracting *Ganoderma lucidum* (Fr.) Karst with water under boiling, concentrating the resulting water extract under reduced pressure, extracting the condensate with an organic solvent and treating the remaining insoluble portion with an aqueous organic solvent to separate said substance "B" as defined in claim 1.

3. A process as claimed in claim 2, wherein the organic solvent is a lower aliphatic alcohol, benzene, xylene, chloroform, ethyl ether or acetone.

4. A process as claimed in claim 2, wherein the aqueous organic solvent is a lower aliphatic alcohol selected from the group consisting of ethanol, methanol or i- or n-butanol.

5. A process as claimed in claim 2, wherein the organic solvent is 98% or more ethanol.

6. A process as claimed in claim 2, wherein the aqueous organic solvent is a mixture of water with a lower aliphatic alcohol, acetone, dioxane, tetrahydrofuran, dimethylformamide or dimethylsulfoxide.

7. A process as claimed in claim 2, wherein the aqueous organic solvent is a lower aliphatic alcohol containing 20~30% water.

8. A process as claimed in claim 2, wherein the aqueous organic solvent is 20~30% aqueous ethanol.

9. A pharmaceutical composition having antitumor activity which comprises the substance as defined in claim 1 and a pharmaceutically acceptable carrier.

10. A composition in accordance with claim 9, in oral dosage unit form.

* * * * *